Figure 1:
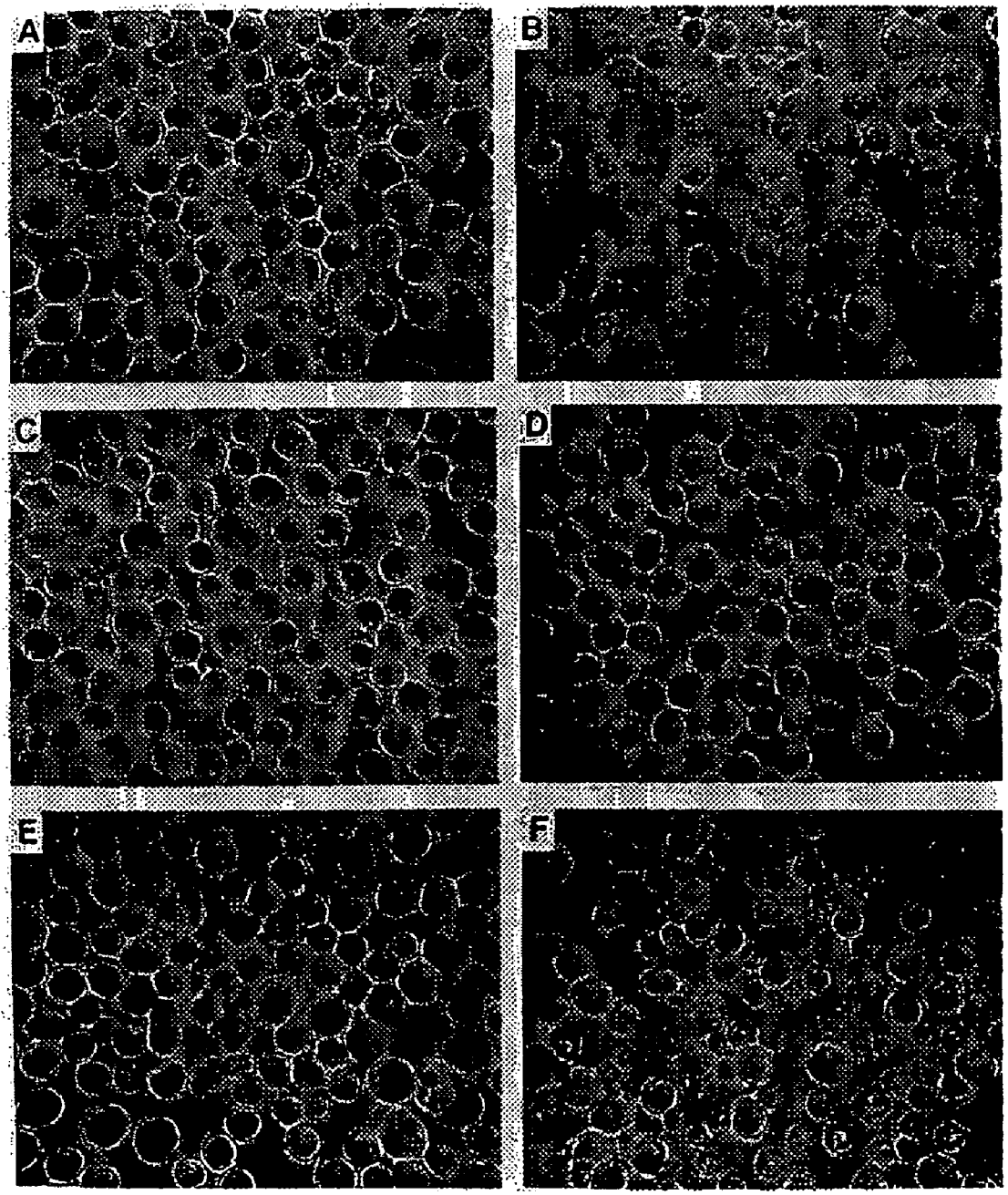

US007608273B2

(12) United States Patent
Kang et al.

(10) Patent No.: US 7,608,273 B2
(45) Date of Patent: Oct. 27, 2009

(54) RECOMBINANT LENTIVIRUS ENCODING MODIFIED GP 120 SIGNAL SEQUENCES

(75) Inventors: Chil-Yong Kang, London (CA); Yan Li, London (CA)

(73) Assignee: University of Western Ontario, London (CA)

( * ) Notice: Subject to any disclaimer, the term of this patent is extended or adjusted under 35 U.S.C. 154(b) by 347 days.

(21) Appl. No.: 11/107,364

(22) Filed: Apr. 15, 2005

(65) Prior Publication Data

US 2005/0271686 A1 Dec. 8, 2005

Related U.S. Application Data

(63) Continuation-in-part of application No. 09/762,294, filed as application No. PCT/CA99/00746 on Aug. 12, 1999, now Pat. No. 7,067,134.

(60) Provisional application No. 60/096,235, filed on Aug. 12, 1998.

(51) Int. Cl.
*A61K 39/21* (2006.01)
*A61K 39/12* (2006.01)

(52) U.S. Cl. ............... 424/208.1; 424/188.1; 424/199.1

(58) Field of Classification Search ....................... None
See application file for complete search history.

(56) References Cited

U.S. PATENT DOCUMENTS 7,067,134 B1 6/2006 Kang et al.

FOREIGN PATENT DOCUMENTS

WO WO 94/17825 8/1994
WO WO 00 09703 2/2000

OTHER PUBLICATIONS

Li, Y., et al., 1994, "Control of expression, glycosylation, and secretion of HIV-1 gp120 by homologous and heterologous signal sequences", Virol. 204:266-278.*

Jamieson, B. D., et al., 1994, "Requirement of human immunodeficiency virus type 1 nef for in vivo replication and pathogenicity", J. Virol. 68(6):3478-3485.*

Haynes, B. F., 1996, "HIV vaccines: where we are and where we are going", The Lancet 348:933-37.*

Burton, D. R., and J. P. Moore, 1998, "Why do we not have an HIV vaccine and how can we make one?", Nat. Med. Vac. Suppl. 4(5):495-98.*

Moore, J. P., and D. R. Burton, 1999, "HIV-1 neutralizing antibodies: how full is the bottle?", Nat. Med. 5(2):142-44.*

Feinberg, M. B., and J. P. Moore, 2002, "AIDS vaccine models: challenging challenge viruses", Nat. Med. 8(3):207-10.*

McMichael, A. J., and T. Hanke, 2003, "HIV vaccines 1983-2003", Nat. Med. 9(7):874-80.*

Desrosiers, R. C., 2004, "Prospects for an AIDS vaccine", Nat. Med. 10(3):221-223.*

Banda, N. K. et al., "Crosslinking, CD4 by human immunodeficiency virus gp120 primes T cells for activation-induced apoptosis", *J. Exp. Med.*, 176(4):1099-1106 (abstract provided)(1992).

Burton, D. R. et al., "Why do we not have an HIV vaccine and how can we make one", *Nat. Med. Vac. Suppl.*, 4(5):495-98 (1998).

Chakrabarti, et al., Proceedings of the National Academy of Sciences of USA, 93(18):9810-9815 (1996).

Daniel, M. D. et al., "Protective effects of a live attenuated SIV vaccine with a deletion in the nef gene", *Science*, 258(5090):1938-41 (abstract provided)(1992).

Haynes, B. F., "HIV Vaccines: where are we and where are we going?", *Lancet*, 348:933-37 (1996).

Haynes, B. F. et al., "Update on the issues of HIV vaccine development", *Ann. Med.*, 28-39-41 (1996).

Jassoy, C. et al., "Human Immunodeficiency virus type 1-specific cytotoxic T lymphocytes . . . ", *J. Virol.*, 67(5):2844-2852 (1989).

Laurent-Crawford, A. G. et al., "Membrane expression of HIV envelope glycoproteins triggers apoptosis in CD4 cells", *AIDS Res. Human Retrovir.*, 9(8):761-773 (abstract provided)(1993).

Lee, T.-H., "Acquired immunodeficiency disease vaccines: design and development", *AIDS: Biology, Diagnosis, Treatment, and Prevention*, DeVita, Jr., V. T., et al., eds., fourth eds., 605-616 (1997).

Letvin, N. L., "Progress in the development of an HIV-1 vaccine", *Science*, 280:1875-1880 (1998).

Li, Y. et al., "Control of expression, glycosylation, and secretion of HIV-1 gp120 by homologous and heterologous signal sequences", *Virol.*, 204:266-278 (1994).

Li, Y. et al., "Effects of inefficient cleavage of the signal sequence of HIV-1 gp120 on its association with calnexin, folding and intracellular transport", *Proc. Natl. Acad. Sci. USA*, 93:9606-9611 (1996).

Siliciano, R. F. et al., "Analysis of host-virus interactions in AIDS with anti-gp120 T cell clones: effect of HIV sequence variation and a mechanism for CD4+ cell depletion", *Cell*, 54(4):561-575 (abstract provided)(1988).

Stevenson, M. et al., "Envelope glycoprotein of HIV induces interference and cytolosis resistance in CD4+ cells: mechanism for persistence in AIDS", *Cell*, 53(3):483-496 (abstract provided)(1988).

Weinhold, K. et al., "HIV-1 gp120-mediated immune suppression and lymphocyte destruction in the absence of viral infection", *J. Immunol.*, 142(9):3091-3097 (abstract provided)(1989).

Daniel, M. D. et al., "Protective Effects of a Live Attenuated SIV Vaccine with a Deletion in the *nef* Gene," Science 258:1938-1941 (1992).

Supplementary European Search Report for EP 06 72 7538 dated Nov. 21, 2008.

* cited by examiner

*Primary Examiner*—Jeffrey S. Parkin
(74) *Attorney, Agent, or Firm*—Foley Hoag LLP

(57) ABSTRACT

Novel HIV vaccines comprising an avirulent and non-cytolytic recombinant HIVs are provided.

13 Claims, 10 Drawing Sheets

FIGURE 2

FIGURE 3
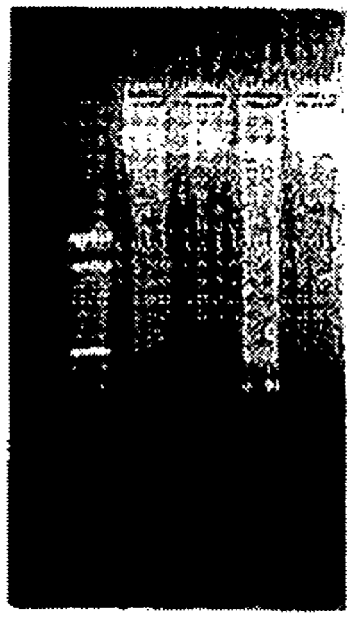
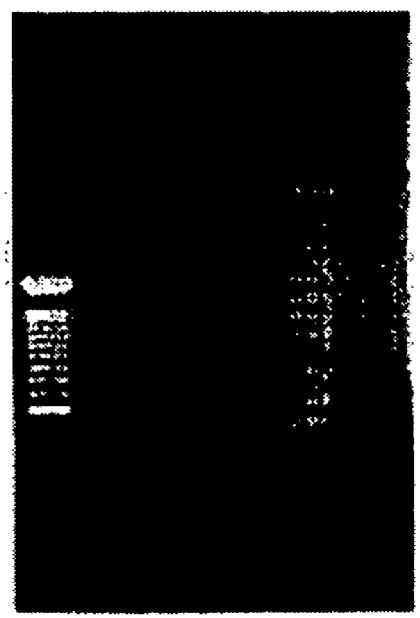

FIGURE 4
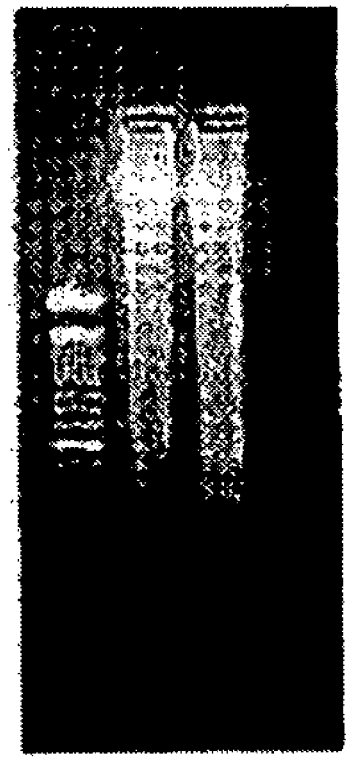 

FIGURE 7
A3.01 Cells
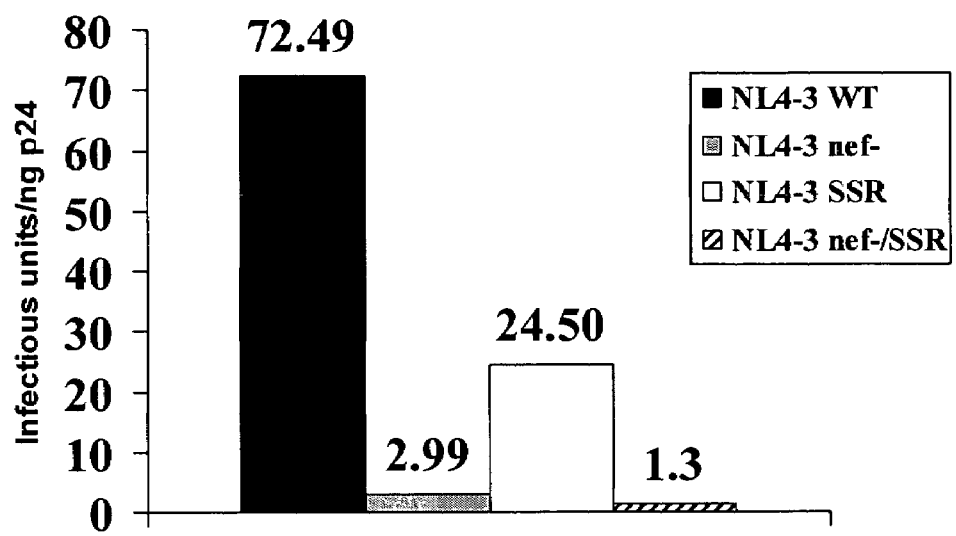
H9 Cells
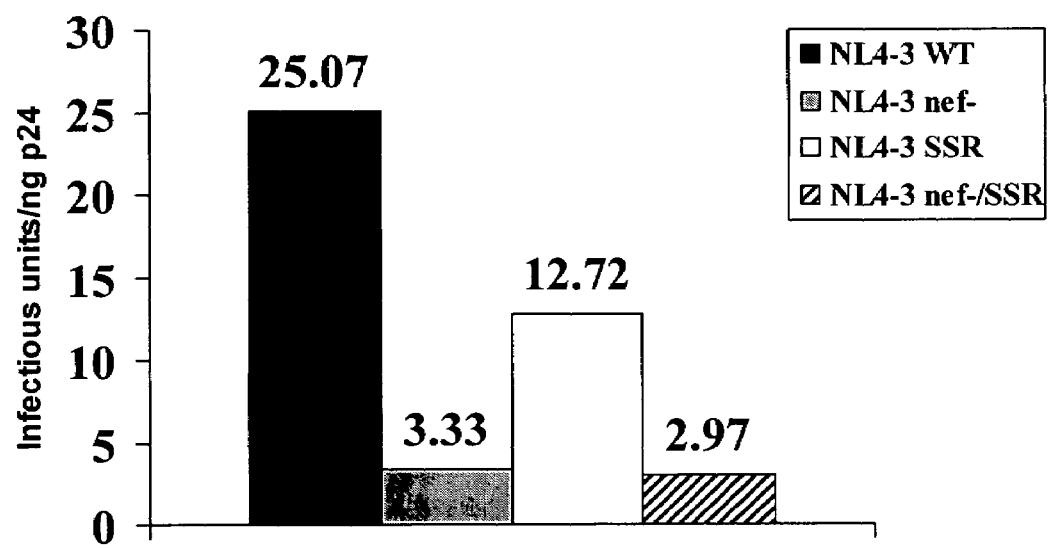

FIGURE 9

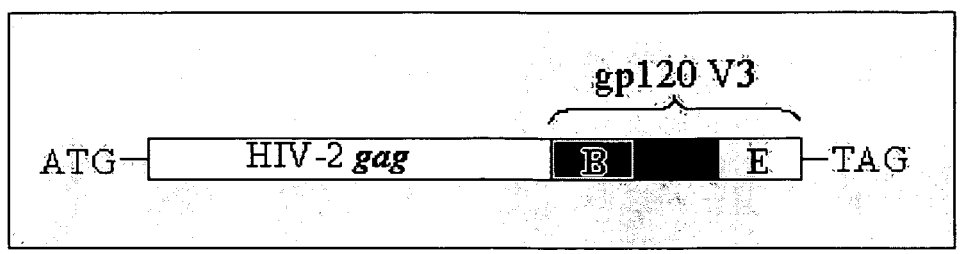

[a] HIV-2 *gag*-V3(BCE) chimeric VLP

Clade B: SIPIGPGRAFYATGD (SEQ ID NO: 27); Clade C: SVRIGPGQTFYATGA (SEQ ID NO: 28); Clade E: SIRIGPGQVFYRTGD (SEQ ID NO: 29)

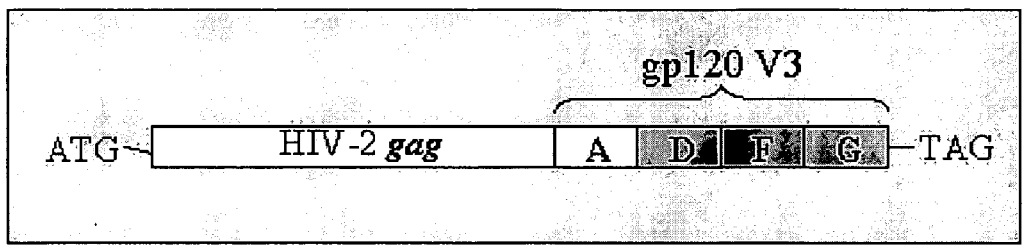

[b] HIV-2 *gag*-V3(ADFG) chimeric VLP

Clade A: SVRIGPGQTFYATGD (SEQ ID NO: 30); Clade D: RTPIGLGQALYTTRD (SEQ ID NO: 31); Clade F: RISLGPGRVFYTAGE (SEQ ID NO: 32); Clade G: SINLGPGQAIYATGA (SEQ ID NO: 33)

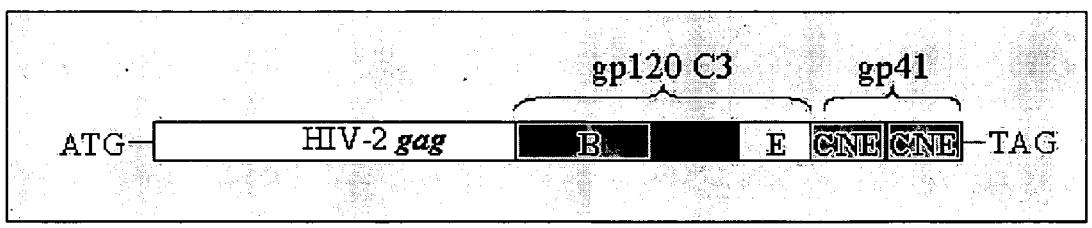

[c] HIV-2 *gag*-C3(BCE)CNE chimeric VLP

Clade B: PCRIKQIVNMWQEVGKAMYAPPISGQIRCSSNITGLLLTRD (SEQ ID NO: 34);
Clade C: RAMYAPPIAGNITCKSNIRS (SEQ ID NO: 35);
Clade E: QAMYAPPISGKIN (SEQ ID NO: 36); Conserved Neutralizing Epitope (CNE) of gp41: ELDKWA (SEQ ID NO: 37)

FIGURE 10
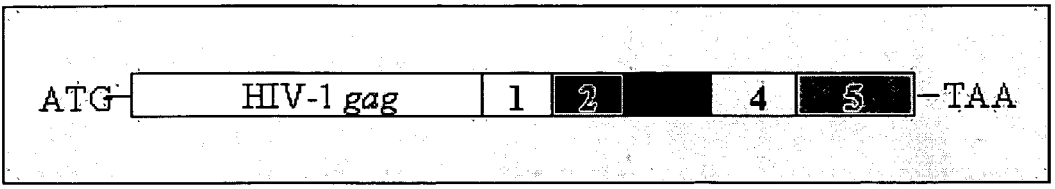
[a] HIV-1 *gag*-TCE chimeric VLP
| #1: gp41HXB2 | (337-345) | IPRRIRQGL (SEQ ID NO: 38) |
| #2: NefHXB2 | (92-100) | KEKGGLDGL (SEQ ID NO: 39) |
| #3: NefHXB2 | (128-137) | TPGPGVRYPL (SEQ ID NO: 40) |
| #4: gp120HXB2 | (584-592) | ERYLKDQQLL (SEQ ID NO: 41) |
| #5: gp120HXB2 | (30-46) | AAENLWVTVYYGVPVWK (SEQ ID NO: 42) |
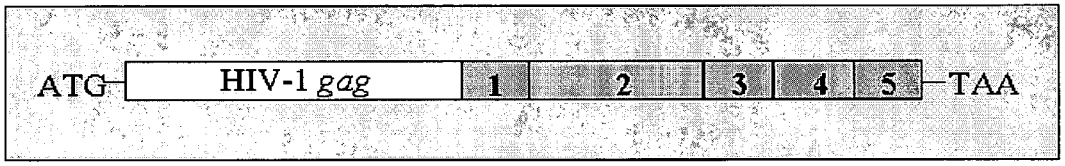
[b] HIV-1 *gag*-TCE chimeric VLP
| #1: RTHXB2 | (309-317) | ILKEPVHGV (SEQ ID NO: 43) |
| #2: RTHXB2 | (171-190) | FRKQNPDIVIYQYMDDLYVG (SEQ ID NO: 44) |
| #3: RTHXB2 | (156-166) | AIFQSSMTK (SEQ ID NO: 45) |
| #4: TatHXB2 | (2-11) | EPVDPRLEPW (SEQ ID NO: 46) |
| #5: RevHXB2 | (69-77) | PAEPVPLQL (SEQ ID NO: 47) |

SEQUENCE LISTING

<160> NUMBER OF SEQ ID NOS: 47

<210> SEQ ID NO 1
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Arg Val Lys Glu Lys Lys Thr Gln His Leu Trp Arg Trp Gly Trp
 1               5                  10                  15

Arg Trp Gly Thr Met Leu Leu Gly Met Leu Met Ile Cys Ser Ala
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Any neutral amino acid
<220> FEATURE:
<221> NAME/KEY: MOD_RES
<222> LOCATION: (4)
<223> OTHER INFORMATION: Any neutral amino acid
<220> FEATURE:
<221> NAME/KEY: MOD_RES
<222> LOCATION: (6)
<223> OTHER INFORMATION: Any neutral amino acid
<220> FEATURE:
<221> NAME/KEY: MOD_RES
<222> LOCATION: (13)
<223> OTHER INFORMATION: Any neutral amino acid
<220> FEATURE:
<221> NAME/KEY: MOD_RES
<222> LOCATION: (17)
<223> OTHER INFORMATION: Any neutral amino acid

<400> SEQUENCE: 2

Met Xaa Val Xaa Glu Xaa Lys Thr Gln His Leu Trp Xaa Trp Gly Trp
 1               5                  10                  15

Xaa Trp Gly Thr Met Leu Leu Gly Met Leu Met Ile Cys Ser Ala
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Arg Val Ala Glu Ile Lys Thr Gln His Leu Trp Arg Trp Gly Trp
 1               5                  10                  15

Arg Trp Gly Thr Met Leu Leu Gly Met Leu Met Ile Cys Ser Ala
            20                  25                  30

<210> SEQ ID NO 4
<211> LENGTH: 31
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 4

Met Ile Val Lys Glu Lys Lys Thr Gln His Leu Trp Ile Trp Gly Trp
 1               5                  10                  15

Ile Trp Gly Thr Met Leu Leu Gly Met Leu Met Ile Cys Ser Ala
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Arg Val Val Glu Ile Lys Thr Gln His Leu Trp Ile Trp Gly Trp
 1               5                  10                  15

Ile Trp Gly Thr Met Leu Leu Gly Met Leu Met Ile Cys Ser Ala
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Val Val Ala Glu Ile Lys Thr Gln His Leu Trp Ile Trp Gly Trp
 1               5                  10                  15

Ile Trp Gly Thr Met Leu Leu Gly Met Leu Met Ile Cys Ser Ala
            20                  25                  30

<210> SEQ ID NO 7
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Met Lys Phe Leu Val Asn Val Ala Leu Val Phe Met Val Val Tyr Ile
 1               5                  10                  15

Ser Tyr Ile Tyr Ala Asp Pro Ile Asn Met
            20                  25

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Leu Leu Leu Leu Leu Met Leu Phe His Leu Gly Leu Gln Ala Ser
 1               5                  10                  15

Ile Ser Gly Arg Asp Pro Ile Asn Met
```

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ggcggatccg gatcaacgtt caccatagtt                               30

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ggcggatcct tactttccaa gtcg                                     24

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
atttcggatc ctataaatat gagagtcgcg gagatatatc atcac              45

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
atttcggatc ctataaatat gatagtcaag gagaaatatc agcacttgtg gatatggggg    60
tggatatggg gc                                                  72

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
atttcggatc ctataaatat gagagtcgtg gagatatatc agcacttgtg gatatggggc    60

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic primer

<400> SEQUENCE: 14

```
atttcggatc ctataaatat gatagtggcg gagatatatc agcacttgtg gatatggggg      60
tggatatggg gc                                                          72
```

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
agcttggatc cttatctttt ttctctctgc tgcacc                                36
```

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
aatacgactc actat                                                       15
```

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

```
ggcgcatgca ctacagatca t                                                21
```

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
ggcgaattct gcaacaactg ctg                                              23
```

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
ggcctgcagt cattaggcac tgtcttctgc tctttc                                36
```

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
ggcctgcagc catggacaga aaaattgttg gtcacagtc                              39

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggcggatccg ttcactaatc gaatgg                                            26

<210> SEQ ID NO 22
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcctgcaga tgaaattctt agtcaacgtt gcccttgttt ttatggtcgt gtacatttct       60
tacatctatg cggatccatg ggcc                                              84

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcctgcaga tgctgctcct gctcctgatg ctcttccacg gactccaagc ttcaatcagt       60
ggcgatccat gggcc                                                        75

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggcggatcct tagcacttat ctgg                                              24

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gccctcgagt cattaatact gctcccaccc                                        30

<210> SEQ ID NO 26
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 26
tcgtcgtttt gtcgttttgt cgtt        24

<210> SEQ ID NO 27
<211> LENGTH: 15
<212> TYPE: PRT
<213> ORGANISM: Human immunodeficiency virus type 1

<400> SEQUENCE: 27

Ser Ile Pro Ile Gly Pro Gly Arg Ala Phe Tyr Ala Thr Gly Asp
 1               5                  10                  15

<210> SEQ ID NO 28
<211> LENGTH: 15
<212> TYPE: PRT
<213> ORGANISM: Human immunodeficiency virus type 1

<400> SEQUENCE: 28

Ser Val Arg Ile Gly Pro Gly Gln Thr Phe Tyr Ala Thr Gly Ala
 1               5                  10                  15

<210> SEQ ID NO 29
<211> LENGTH: 15
<212> TYPE: PRT
<213> ORGANISM: Human immunodeficiency virus type 1

<400> SEQUENCE: 29

Ser Ile Arg Ile Gly Pro Gly Gln Val Phe Tyr Arg Thr Gly Asp
 1               5                  10                  15

<210> SEQ ID NO 30
<211> LENGTH: 15
<212> TYPE: PRT
<213> ORGANISM: Human immunodeficiency virus type 1

<400> SEQUENCE: 30

Ser Val Arg Ile Gly Pro Gly Gln Thr Phe Tyr Ala Thr Gly Asp
 1               5                  10                  15

<210> SEQ ID NO 31
<211> LENGTH: 15
<212> TYPE: PRT
<213> ORGANISM: Human immunodeficiency virus type 1

<400> SEQUENCE: 31

Arg Thr Pro Ile Gly Leu Gly Gln Ala Leu Tyr Thr Thr Arg Asp
 1               5                  10                  15

<210> SEQ ID NO 32
<211> LENGTH: 15
<212> TYPE: PRT
<213> ORGANISM: Human immunodeficiency virus type 1

<400> SEQUENCE: 32

Arg Ile Ser Leu Gly Pro Gly Arg Val Phe Tyr Thr Ala Gly Glu
 1               5                  10                  15

<210> SEQ ID NO 33
<211> LENGTH: 15
<212> TYPE: PRT
<213> ORGANISM: Human immunodeficiency virus type 1

```
<400> SEQUENCE: 33

Ser Ile Asn Leu Gly Pro Gly Gln Ala Ile Tyr Ala Thr Gly Ala
 1               5                  10                  15

<210> SEQ ID NO 34
<211> LENGTH: 41
<212> TYPE: PRT
<213> ORGANISM: Human immunodeficiency virus type 1

<400> SEQUENCE: 34

Pro Cys Arg Ile Lys Gln Ile Val Asn Met Trp Gln Glu Val Gly Lys
 1               5                  10                  15

Ala Met Tyr Ala Pro Pro Ile Ser Gly Gln Ile Arg Cys Ser Ser Asn
            20                  25                  30

Ile Thr Gly Leu Leu Leu Thr Arg Asp
        35                  40

<210> SEQ ID NO 35
<211> LENGTH: 20
<212> TYPE: PRT
<213> ORGANISM: Human immunodeficiency virus type 1

<400> SEQUENCE: 35

Arg Ala Met Tyr Ala Pro Pro Ile Ala Gly Asn Ile Thr Cys Lys Ser
 1               5                  10                  15

Asn Ile Arg Ser
            20

<210> SEQ ID NO 36
<211> LENGTH: 13
<212> TYPE: PRT
<213> ORGANISM: Human immunodeficiency virus type 1

<400> SEQUENCE: 36

Gln Ala Met Tyr Ala Pro Pro Ile Ser Gly Lys Ile Asn
 1               5                  10

<210> SEQ ID NO 37
<211> LENGTH: 6
<212> TYPE: PRT
<213> ORGANISM: Human immunodeficiency virus type 1

<400> SEQUENCE: 37

Glu Leu Asp Lys Trp Ala
 1               5

<210> SEQ ID NO 38
<211> LENGTH: 9
<212> TYPE: PRT
<213> ORGANISM: Human immunodeficiency virus type 1

<400> SEQUENCE: 38

Ile Pro Arg Arg Ile Arg Gln Gly Leu
 1               5

<210> SEQ ID NO 39
<211> LENGTH: 9
<212> TYPE: PRT
<213> ORGANISM: Human immunodeficiency virus type 1

<400> SEQUENCE: 39

Lys Glu Lys Gly Gly Leu Asp Gly Leu
 1               5
```

<210> SEQ ID NO 40
<211> LENGTH: 10
<212> TYPE: PRT
<213> ORGANISM: Human immunodeficiency virus type 1

<400> SEQUENCE: 40

Thr Pro Gly Pro Gly Val Arg Tyr Pro Leu
 1               5                  10

<210> SEQ ID NO 41
<211> LENGTH: 10
<212> TYPE: PRT
<213> ORGANISM: Human immunodeficiency virus type 1

<400> SEQUENCE: 41

Glu Arg Tyr Leu Lys Asp Gln Gln Leu Leu
 1               5                  10

<210> SEQ ID NO 42
<211> LENGTH: 17
<212> TYPE: PRT
<213> ORGANISM: Human immunodeficiency virus type 1

<400> SEQUENCE: 42

Ala Ala Glu Asn Leu Trp Val Thr Val Tyr Tyr Gly Val Pro Val Trp
 1               5                  10                  15

Lys

<210> SEQ ID NO 43
<211> LENGTH: 9
<212> TYPE: PRT
<213> ORGANISM: Human immunodeficiency virus type 1

<400> SEQUENCE: 43

Ile Leu Lys Glu Pro Val His Gly Val
 1               5

<210> SEQ ID NO 44
<211> LENGTH: 20
<212> TYPE: PRT
<213> ORGANISM: Human immunodeficiency virus type 1

<400> SEQUENCE: 44

Phe Arg Lys Gln Asn Pro Asp Ile Val Ile Tyr Gln Tyr Met Asp Asp
 1               5                  10                  15

Leu Tyr Val Gly
            20

<210> SEQ ID NO 45
<211> LENGTH: 9
<212> TYPE: PRT
<213> ORGANISM: Human immunodeficiency virus type 1

<400> SEQUENCE: 45

Ala Ile Phe Gln Ser Ser Met Thr Lys
 1               5

<210> SEQ ID NO 46
<211> LENGTH: 10
<212> TYPE: PRT
<213> ORGANISM: Human immunodeficiency virus type 1

<400> SEQUENCE: 46

-continued

```
Glu Pro Val Asp Pro Arg Leu Glu Pro Trp
  1               5                  10

<210> SEQ ID NO 47
<211> LENGTH: 9
<212> TYPE: PRT
<213> ORGANISM: Human immunodeficiency virus type 1

<400> SEQUENCE: 47

Pro Ala Glu Pro Val Pro Leu Gln Leu
  1               5
```

RECOMBINANT LENTIVIRUS ENCODING MODIFIED GP 120 SIGNAL SEQUENCES

1. RELATED APPLICATIONS

This application is a continuation-in part application of pending U.S. application Ser. No. 09/762,294, filed Apr. 2, 2001; which claims the benefit of the filing date of International Application No. PCT/CA99/00746, filed Aug. 12, 1999; which claims the benefit of the filing date of U.S. Provisional Application No. 60/096,235, filed Aug. 12, 1998; the contents of all of which are specifically incorporated herein by reference.

2. FIELD OF THE INVENTION

The invention relates to a novel vaccine for use in the prevention and/or treatment of AIDS as well as methods for production thereof. More particularly the invention relates to production of the AIDS virus in large quantities for formulation of an HIV/AIDS vaccine which is non-cytolytic and avirulent.

3. BACKGROUND OF THE INVENTION

Despite recent advances in antiviral therapy, there is no permanent cure for AIDS or HIV infection. Drug therapy, is a promising arena of investigation in terms of providing effective therapy, however because of side effects, compliance, and expense, progress has not been rapid. Compounding these difficulties is the fact that the availability of such drugs is limited in developing countries where it is estimated that the vast majority of new HIV infections will occur.

Due to the success that vaccines to infectious diseases have had, the most notable being against small pox and polio, the search for an effective vaccine against AIDS continues. A variety of approaches have been tried. Indeed, most HIV-1 vaccine development has concentrated on subunit vaccines. The difficulty with the subunit vaccine approach has been the ability to produce optimal immunity. At present, it is not known exactly which components of the HIV antigen(s) and the immune system are necessary for protection from natural infection.

The preferred route for developing vaccines in general is to use whole, inactivated or attenuated viruses, such as the inactivated polio virus vaccine, or attenuated live virus vaccines, such as oral polio vaccine. Unfortunately, this approach can be problematic as shown by the "Cutter incident" in which inadequate inactivation of the polio vaccine resulted in vaccine-mediated transmission of clinical polio.

Early vaccine trials have looked at recombinant subunit protein based immunogens, such as the HIV-1 envelope glycoprotein 120 (gp120). The majority of results from this approach have been disappointing, although immunization regimens that employ both live recombinant virus and subunit protein have, in some individuals, elicited both envelope specific CD8+CTL and neutralizing antibody to the HIV-1 envelope (Cooney, E. L. et al. Proc. Natl. Acad. Sci. USA 90: 1882-86 (1993); McElrath, M. J. et al. J. Infect. Dis. 169: 41-47 (1994); Graham, B. S. et al. J. Infect. Dis. 166: 244-52 (1992); and Graham, B. S. et al. J. Infect. Dis. 167: 533-37 (1993)).

Interestingly, the signal sequence of HIV-1 gp120, which is referred to as the NSS (natural signal sequence), has been found to be associated with the extent of secretion of gp120. It has been shown that substitution of the NSS with either the honey bee mellitin or murine interlukin-3 (IL-3) signal sequence renders a high level production and efficient secretion of gp120 (Li, Y. et al. Virology 204: 266-278 (1994); and Li, Y. et al. Proc. Natl. Acad. Sci. 93: 9606-9611 (1996)). However, it is not known whether the signal sequence of HIV-1 gp120 has a role to play in the pathogenicity of the virus.

With respect to HIV vaccines, it has been shown that deletion of the HIV nef gene attenuates the virus. Desrosiers and his associates have demonstrated that vaccination of Rhesus macaques with nef deleted SIV protected wild-type SIV challenge (Daniels, M. D. et al. Science 258: 1938 (1992); Desrosiers, R. C. et al. Proc. Natl. Acad. Sci. USA 86: 6353 (1989)) and others have demonstrated that the nef gene is dispensable for SIV and HIV replication (Daniels, M. D. et al. Science 258: 1938 (1992); Gibbs, J. S., et al. AIDS Res. and Human Retroviruses 10: 343 (1994); Igarashi, T. et al. J. Gen. Virol. 78: 985 (1997); Kestler III, H. W. et al. Cell 65: 651 (1991)). Furthermore, deletion of the nef gene has been found to render the virus non-pathogenic in the normally susceptible host (Daniels, M. D. et al. Science 258: 1938 (1992)). This deletion, however, has not been found to provide a form of the virus which can be produced in large quantities.

Consequently, a vaccine which is avirulent and can be produced in large quantities is needed.

4. SUMMARY OF THE INVENTION

One aspect of the present invention relates to a recombinant human immunodeficiency virus-1 (HIV-1), wherein the signal sequence of the HIV-1 envelope glycoprotein 120 (gp120) of said virus is a polypeptide sequence listed as SEQ ID NO 3, 4, 5 or 6, or a functional fragment or variant thereof. In certain embodiments said functional fragment or variant contains no more than one (1) positively charged amino acid. In other embodiments, the signal sequence contains no positively charged amino acids. In other embodiments, the virus is rendered avirulent by deletion of a sufficient amount of the nef gene.

Another aspect of the present invention relates to a vaccine comprising a recombinant human immunodeficiency virus. In certain embodiments, the vaccine further comprises an adjuvant. The invention also features methods of preventing or treating a lentiviral infection in a patient comprising administering to a patient in need thereof, an effective amount of any one of the aforementioned vaccines.

Further features and advantages of the present invention will become apparent from the following detailed description and claims.

5. BRIEF DESCRIPTION OF THE DRAWINGS

FIG. 1 contains photographs of phase-contrast microscopic examinations of wild-type and recombinant baculovirus infected S. frugiperda insect cells (SF21). Panel A depicts cells infected with wild-type Autographica californica Nuclear Polyhedrosis virus (AcNPV), wherein intact cells are observed; Panel B depicts cells infected with recombinant AcNPV which express Human Immunodeficiency Virus-1 (HIV-1) envelope glycoprotein 120 with its natural signal sequence (vAc-gp120-NS), wherein cell lysis is observed; Panel C depicts cells infected with recombinant AcNPV that express HIV-1 envelope gp120 without its natural signal sequence (vAc-gp120-ΔS), wherein intact cells are observed; Panel D depicts cells infected with recombinant AcNPV that express HIV-1 envelope gp120 wherein the natural signal sequence is replaced by a mellitin signal sequence (vAc-gp120-MS), wherein intact cells are observed; Panel E depicts cells infected with recombinant AcNPV that express vesicular stomatitis virus glycoprotein G (vAc-VSV-G), wherein intact cells are observed; Panel F depicts cells infected with recombinant AcNPV that express vesicular stomatitis virus glycoprotein G (VSV-G) with the natural signal sequence of HIV-1 glycoprotein 120 appended (vAcVSV-G-NS), wherein cell lysis is observed.

Figure 2:
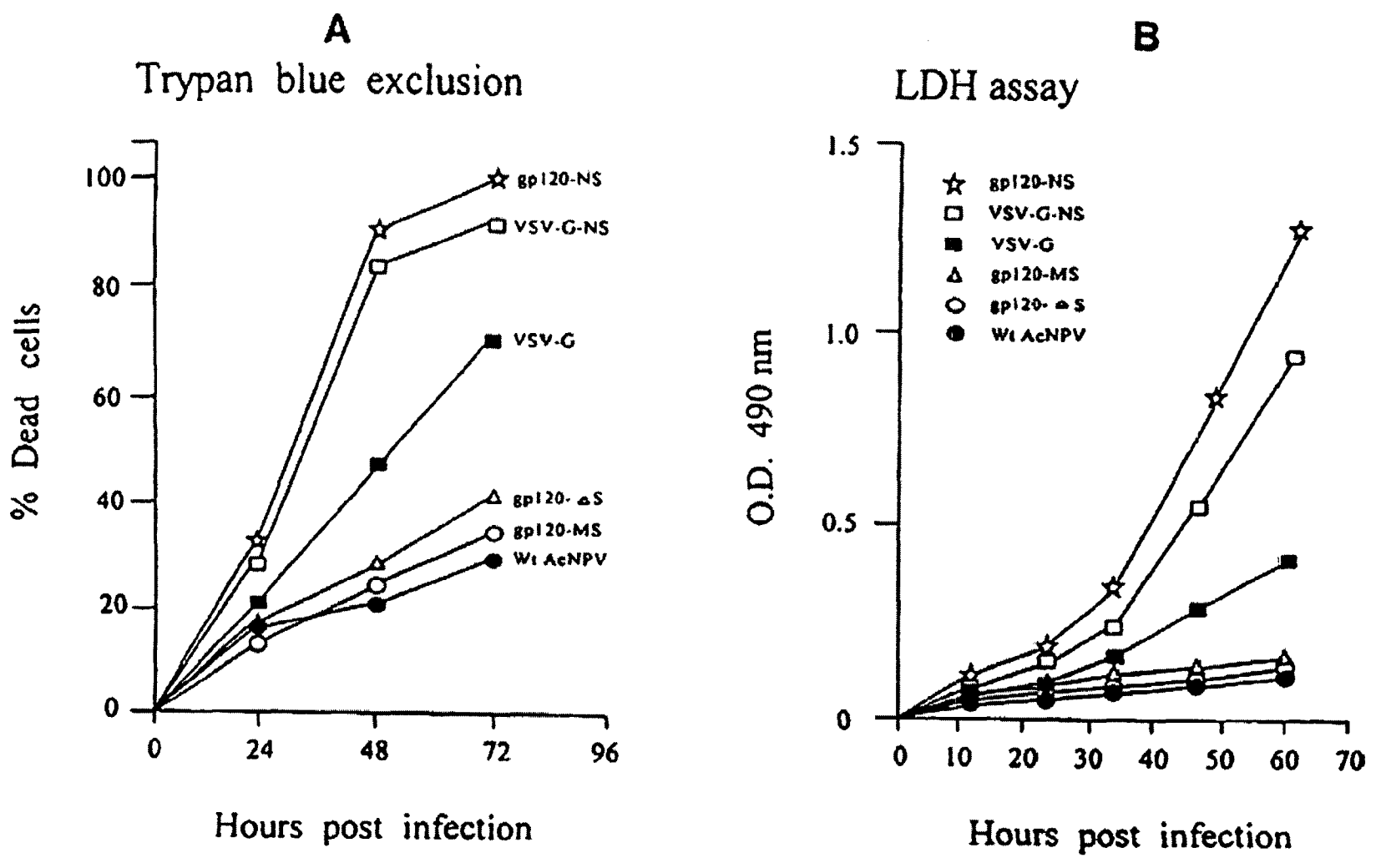

FIG. 2 provides graphs illustrating the effects of HIV-1 envelope glycoprotein 120 (gp120) signal sequence on cell death. FIG. 2A depicts the percentage of cells permeablized by trypan blue (dead cells) after expressing a recombinant glycoprotein (rgp120) or vesicular stomatitis virus glycoprotein G (VSV-G) protein with different signal sequences. FIG. 2B depicts the results of a lactate dehydrogenase (LDH) release assay (Boehringer Mannheim's Cytotoxicity Detection Kit). The amounts of LDH released from SF21 cells infected with recombinant viruses expressing a rgp120 or a VSV-G with different signal sequences was measured by quantitating the formazan dye formed in ELISA plates read at 490 nm.

FIG. 3 depicts agarose gel electrophoresis results providing an analysis of DNA fragmentation of *S. frugiperda* insect cells (SF21) infected with an *Autographica californica*-Nuclear Polyhedrosis virus (AcNPV) expressing HIV-1 envelope glycoprotein 120 with different signal sequences. Total cellular DNA (A) or low molecular weight DNA (B) was extracted at 48 hours post infection and analyzed by 1.2% agarose gel electrophoresis in the presence of ethidium bromide; Lanes M: DNA marker; Lanes WT: cells infected with AcNPV; Lanes ΔS: cells infected with an AcNPV recombinant that expresses an HIV-1 envelope glycoprotein 120 with its natural signal sequence removed (vAc-gp120-ΔS); Lane NS: cells infected with an AcNPV recombinant that expresses an HIV-1 envelope glycoprotein 120 with its natural signal sequence intact (vAc-gp120-NS); Lanes MS: depicts cells infected with an AcNPV recombinant that express an HIV-1 envelope glycoprotein 120 with its natural signal sequence replaced by a honey bee mellitin signal sequence (vAc-gp120-MS).

FIG. 4 depicts agarose gel electrophoresis results providing an analysis of DNA fragmentation of *S. frugiperda* insect cells (SF21) infected with recombinant *Autographica californica* Nuclear Polyhedrosis virus (AcNPV) expressing vesicular stomatitis virus glycoprotein G (VSV-G) with or without the HIV-1 envelope glycoprotein 120 (gp120) natural signal sequence. Total cellular DNA (A) or low molecular weight DNA (B) was extracted at 48 hours post infection and analyzed by 1.2% agarose gel electrophoresis in the presence of ethidium bromide; Lanes M: DNA marker; Lanes VSV-G: cells infected with an AcNPV recombinant that express an unmodified vesicular stomatitis virus glycoprotein G; Lanes VSV-G-NS: cells infected with an AcNPV recombinant that express a vesicular stomatitis virus glycoprotein G, modified to contain the HIV-1 envelope gp120 natural signal sequence (vAcVSV-G-NS).

Figure 5:
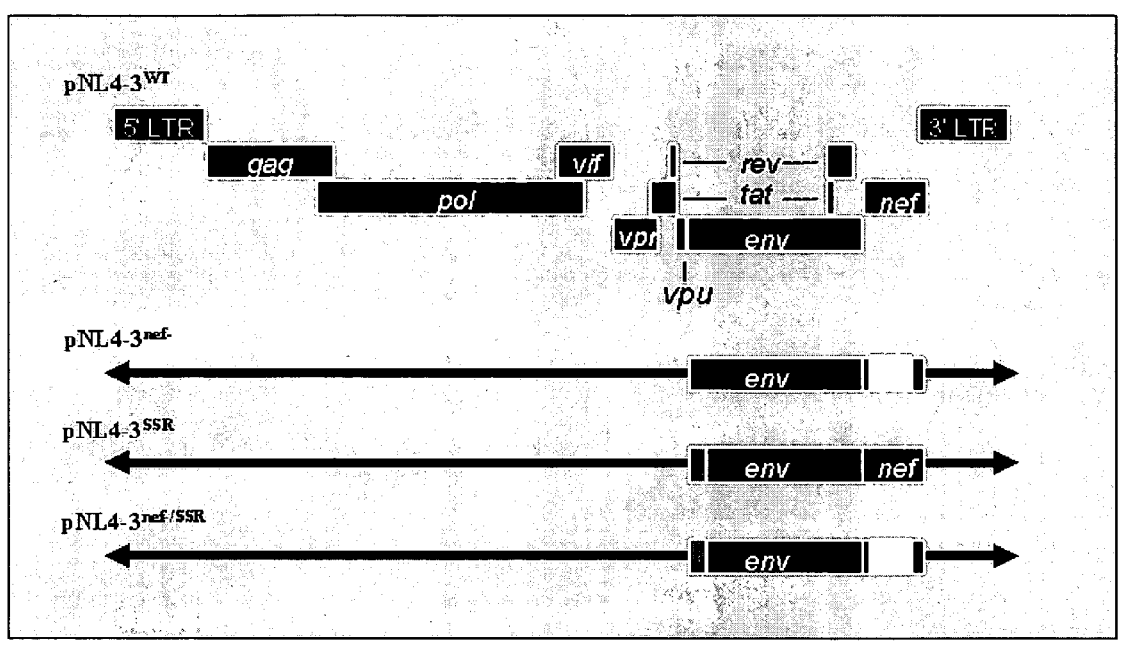

FIG. 5 depicts the construction of genetically modified HIV-1 proviral clones. Using the HIV-1 clade B provirus, pNL4-3, as the backbone vector, 3 genetically modified forms of the virus were prepared. These include pNL4-3$^{nef-}$, which contains a targeted deletion of the nef gene, pNL4-3$^{SSR}$, which has had the natural Env glycoprotein signal sequence replaced with the honeybee mellitin signal sequence, and pNL4-3$^{nef-/SSR}$, which contains a combination of both the nef deletion and signal sequence replacement mutations. The pNL4-3$^{WT}$ plasmid represents the parental, wild-type provirus.

Figure 6:
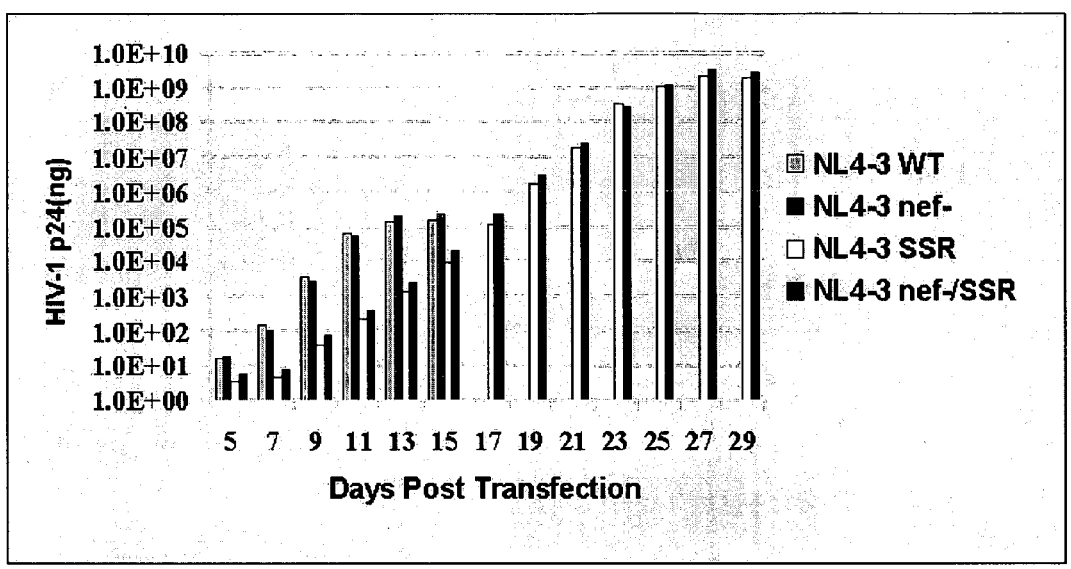

FIG. 6 depicts a graph showing that prolonged cell survival leads to increased virus yield in A3.01 cells. Genetically modified HIV-1 clade B virus include NL4-3$^{nef-}$, which contains a targeted deletion of the nef gene, NL4-3$^{SSR}$, which has had the natural Env glycoprotein signal sequence replaced with the honeybee mellitin signal sequence, NL4-3$^{nef-/SSR}$, which contains a combination of both the nef deletion and signal sequence replacement mutations, and NL4-3$^{WT}$, which represents the parental, wild-type provirus.

FIG. 7 depicts the infectivity of HIV-1 NL4-3 mutants in A3.01 and H9 cells using the MAG1 assay. Genetically modified HIV-1 clade B virus include NL4-3$^{nef-}$, which contains a targeted deletion of the nef gene, NL4-3$^{SSR}$, which has had the natural Env glycoprotein signal sequence replaced with the honeybee mellitin signal sequence, NL4-3$^{nef-/SSR}$, which contains a combination of both the nef deletion and signal sequence replacement mutations, and NL4-3 $^{WT}$, which represents the parental, wild-type provirus.

Figure 8:
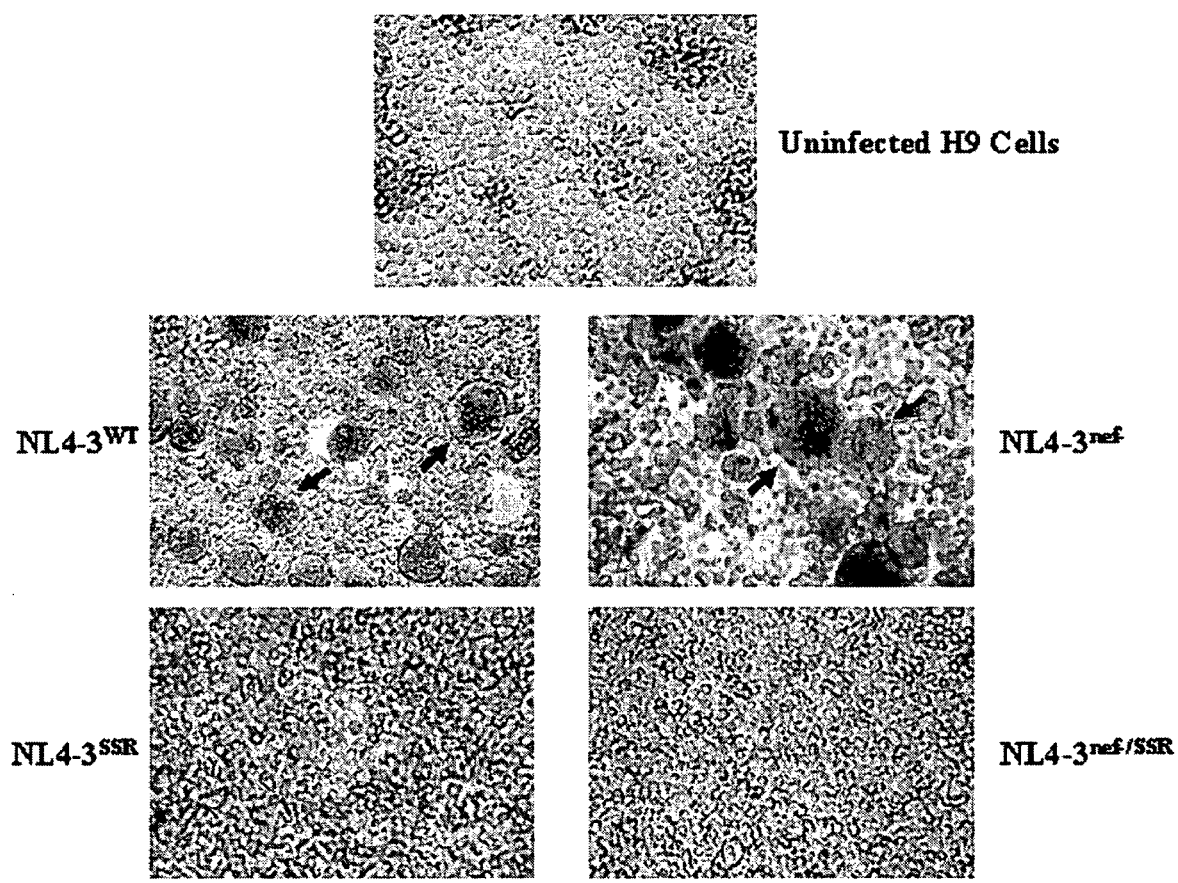

FIG. 8 depicts the induction of cytopathic effect (syncytium formation) by HIV-1$_{NL4-3}$ in H9 infected cells. Genetically modified HIV-1 clade B virus include NL4-3$^{nef-}$, which contains a targeted deletion of the nef gene, NL4-3, which has had the natural Env glycoprotein signal sequence replaced with the honeybee mellitin signal sequence, NL4-3$^{nef-/SSR}$, which contains a combination of both the nef deletion and signal sequence replacement mutations, and NL4-3 WT, which represents the parental, wild-type provirus.

FIG. 9 depicts the construction of gag-NE chimeric genes which will carry the HIV gag gene with several distinct V3 coding sequences with or without conserved neutralizing epitopes of major HIV-1 clades. FIG. 9a consists of HIV-2 gag gene with V3 domains from HIV-1 clades B (SEQ ID NO: 27), C (SEQ ID NO: 28) and E (SEQ ID NO: 29), and FIG. 9b consists of HIV-2 gag gene with V3 domains from HIV-1 clades A (SEQ ID NO: 30), D (SEQ ID NO: 31), F (SEQ ID NO: 32) and G (SEQ ID NO: 33). In figure 9c, epitopes from gp1120 representing a constant region, C3, from clades B (SEQ ID NO: 34), C (SEQ ID NO: 35) and E (SEQ ID NO: 36), as well as the conserved neutralizing epitope (CNE) of gp41 (SEQ ID NO: 37) represented by 6 amino acids (Muster, et al., J. Virol. 67: 6642, 1993), have been selected to make neutralizing antibodies which will cross-react with the majority of HIV-1 isolates.

FIG. 10 depicts the construction of a gag-TCE chimeric gene with multiple cytotoxic T-cell epitopes (TCE) from gp41, Nef, gp1120, reversetranscriptase (RT), Tat and Rev protiens of HIV-1 clade B (SEQ ID NOS: 38-47).

6. DETAILED DESCRIPTION OF THE INVENTION

1. Definitions

For convenience, the meaning of certain terms and phrases employed in the specification, examples, and appended claims are provided below. Unless defined otherwise, all technical and scientific terms used herein have the same meaning as commonly understood by one of ordinary skill in the art to which this invention belongs.

The articles "a" and "an" are used herein to refer to one or more than one (i.e., to at least one) of the grammatical object of the article.

The term "amino acid" is known in the art. In general the abbreviations used herein for designating the amino acids and the protective groups are based on recommendations of the IUPAC-IUB Commission on Biochemical Nomenclature (see Biochemistry (1972) 11: 1726-1732). In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan.

The term "amino acid" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1 methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (d) and (l) stereoisomers of such amino acids when the structure of the amino acid admits of stereoisomeric forms. The configuration of the amino acids and amino acid residues herein are designated by the appropriate symbols (d), (l) or (dl), furthermore when the configuration is not designated the amino acid or residue can have the configuration (d), (l) or (dl). It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (d) or (l) stereoisomers.

The term "antibody" as used herein is intended to include whole antibodies, e.g., of any isotype (IgG, IgA, IgM, IgE, etc), including polyclonal, monoclonal, recombinant and humanized antibodies and fragments thereof which specifically recognize and are able to bind an epitope of a protein. Antibodies can be fragmented using conventional techniques and the fragments screened for utility in the same manner. Thus, the term includes segments of proteolytically-cleaved or recombinantly-prepared portions of an antibody molecule that are capable of selectively reacting with a certain protein. Nonlimiting examples of such proteolytic and/or recombinant fragments include Fab, F(ab')2, Fab', Fv, and single chain antibodies (scFv) containing a V[L] and/or V[H] domain joined by a peptide linker. The scFvs may be covalently or non-covalently linked to form antibodies having two or more binding sites.

The term "conservative substitutions" refers to changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; valine-leucine-isoleucine-methionine; phenylalanine-tyrosine; phenylalanine-tyrosine-tryptophan; lysine-arginine; and histidine-lysine-arginine.

The term "essentially noncytolytic" as used herein means that the retrovirus does not significantly damage or kill the cells it infects.

"Equivalent" when used to describe nucleic acids or nucleotide sequences refers to nucleotide sequences encoding functionally equivalent polypeptides. Equivalent nucleotide sequences will include sequences that differ by one or more nucleotide substitution, addition or deletion, such as an allelic variant; and will, therefore, include sequences that differ due to the degeneracy of the genetic code. For example, nucleic acid variants may include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions.

Variant peptides may be covalently prepared by direct chemical synthesis using methods well known in the art. Variants may further include, for example, deletions, insertions or substitutions of residues within the amino acid sequence. Any combination of deletion, insertion, and substitution may also be made to arrive at the final construct, provided that the final construct possesses the desired activity. These variants may be prepared by site-directed mutagenesis, (as exemplified by Adelman et al., DNA 2: 183 (1983)) of the nucleotides in the DNA encoding the peptide molecule thereby producing DNA encoding the variant and thereafter expressing the DNA in recombinant cell culture. The variants typically exhibit the same qualitative biological activity as wild type polypeptides. It is known in the art that one may also synthesize all possible single amino acid substitutions of a known polypeptide (Geysen et al., Proc. Nat. Acad. Sci. (USA) 18:3998-4002 (1984)). While the effects of different substitutions are not always additive, it is reasonable to expect that two favorable or neutral single substitutions at different residue positions in a polypeptide can safely be combined without losing any protein activity. Methods for the preparation of degenerate polypeptides are as described in Rutter, U.S. Pat. No. 5,010,175; Haughter et al., Proc. Nat. Acad. Sci. (USA) 82:5131-5135 (1985); Geysen et al., Proc. Nat. Acad. Sci. (USA) 18:3998-4002 (1984); WO86/06487; and WO86/00991.

In devising a substitution strategy, a person of ordinary skill would determine which residues to vary and which amino acids or classes of amino acids are suitable replacements. One may also take into account studies of sequence variations in families or naturally occurring homologous proteins. Certain amino acid substitutions are more often tolerated than others, and these are often correlated with similarities in size, charge, etc., between the original amino acid and its replacement. Insertions or deletions of amino acids may also be made, as described above. The substitutions are preferably conservative, see, e.g., Schulz et al., Principle of Protein Structure (Springer-Verlag, New York (1978)); and Creighton, Proteins: Structure and Molecular Properties (W.H. Freeman & Co., San Francisco (1983)); both of which are hereby incorporated by reference in their entireties.

A "functional" fragment of a nucleic acid as used herein is a nucleic acid fragment capable of coding for a signal sequence for a gene linked to the fragment. Thus, a "functional fragment" of a nucleic acid is intended to include nucleic acids capable of coding for a signal sequence in appropriate conditions.

The term "HIV" is known to one skilled in the art to refer to Human Immunodeficiency Virus. There are two types of HIV: HIV-1 and HIV-2. There are many different strains of HIV-1. The strains of HIV-1 can be classified into three groups: the "major" group M, the "outlier" group O and the "new" group N. These three groups may represent three separate introductions of simian immunodeficiency virus into humans. Within the M-group there are at least ten subtypes or clades: e.g., clade A, B, C, D, E, F, G, H, I, J, and K. A "clade" is a group of organisms, such as a species, whose members share homologous features derived from a common ancestor. Any reference to HIV-1 in this application includes all of these strains.

The terms "polynucleotide", and "nucleic acid" are used interchangeably to refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "recombinant" polynucleotide means a polynucleotide of genomic, cDNA, semi-synthetic, or synthetic origin, which either does not occur in nature or is linked to another polynucleotide in a non-natural arrangement. An "oligonucleotide" refers to a single stranded polynucleotide having less than about 100 nucleotides, less than about, e.g., 75, 50, 25, or 10 nucleotides.

The terms "polypeptide", "peptide" and "protein" (if single chain) are used interchangeably herein to refer to polymers of amino acids. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In certain embodiments, polypeptides of the invention may be synthesized chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted religation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

As known to one skilled in the art, "retroviruses" are diploid positive-strand RNA viruses that replicate through an integrated DNA intermediate (proviral DNA). In particular, upon infection by the RNA virus, the lentiviral genome is reverse-transcribed into DNA by a virally encoded reverse transcriptase that is carried as a protein in each retrovirus. The viral DNA is then integrated pseudo-randomly into the host cell genome of the infecting cell, forming a "provirus" which is inherited by daughter cells. The retrovirus genome contains at least three genes: gag codes for core and structural proteins of the virus; pol codes for reverse transcriptase, protease and integrase; and env codes for the virus surface proteins. Within the retrovirus family, HIV is classified as a lentivirus, having genetic and morphologic similarities to animal lentiviruses such as those infecting cats (feline immunodeficiency virus), sheep (visna virus), goats (caprine arthritis-encephalitis virus), and non-human primates (simian immunodeficiency virus).

As used herein, "sufficient deletion" means deletion of enough of a nucleic acid sequence to prevent transcription and thereby production of the corresponding protein product.

2. Overview

The present invention is based at least in part on the surprising finding that replacement of the natural signal sequence (NSS) of the envelope glycoprotein gp120 of HIV-1 with a signal sequence which contains no more than one positively charged amino acid results in a modified HIV-1, which is non-cytolytic and as such is capable of highly efficient synthesis, glycosylation, and secretion of gp120. In particular, it was observed that the alteration of positively charged amino acid residues in the gp120 signal sequence not only increased the level of expression but also the level of secretion. The level of secretion was increased as the amount of positive charge was reduced. In contrast, the removal of all five positively charged amino acid residues in HIV-1 clade B gp120 signal sequence resulted in large quantities of the non-glycosylated form of gp120 accumulating in the cells. This result indicated that a minimum number of positively charged amino acid residues is required for efficient translocation of the protein across the ER membrane.

3. Recombinant Lentivirus

In one aspect, the present invention provides an essentially noncytolytic recombinant HIV-1 capable of highly efficient replication wherein the NSS of the virus' envelope glycoprotein is replaced with a signal sequence of about 20 to about 40 amino acids in length wherein said signal sequence contains no more than one (1) positively charged amino acids.

The modified gp120 signal sequence can be made by substituting neutral amino acids for positively charged amino acids in the natural signal sequence (MRVKEKKTQHLWRWGWRWGTMLLGMLMICSA; SEQ ID NO: 1); such modifications can be represented as: $MX_1VX_2EX_3KTQHLWX_4WGWX_5WGTMLLGMLMICSA$ (SEQ ID NO: 2) wherein $X_1$, $X_2$, $X_3$, $X_4$, and $X_5$ are neutral amino acids. Positively charge residues are shown in bold and underlined.

Exemplary modified signal sequences include:

MRVAEIKTQHLWRWGWRWGTMLLGMLMICSA (YL-1; SEQ ID NO: 3),

MIVKEKKTQHLWIWGWIWGTMLLGMLMICSA (YL-2; SEQ ID NO: 4),

MRVVEIKTQHLWIWGWIWGTMLLGMLMICSA (YL-3; SEQ ID NO: 5),

MIVAEIKTQHLWIWGWIWGTMLLGMLMICSA (YL-4; SEQ ID NO: 6),

MKFLVNVALVFMVVYISYIYADPINM (modified mellitin signal peptide, the underlined sequence is a result of linker insertion and indicates five amino acids between the signal sequence and the mature gp120 protein; SEQ ID NO: 7), MLLLLLMLFHLGLQASISGRDPINM (modified interleukin 3 signal peptide, the underlined sequence is a result of linker insertion and indicates seven amino acids between the signal sequence and the mature gp120 protein; SEQ ID NO: 8), or a functional fragment or variant thereof.

4. Vaccines of the Invention

The present invention further features vaccines comprising an effective amount of an avirulent and an essentially non-cytolytic lentivirus as described above.

The vaccine compositions of the invention are suitable for administration to subjects in a biologically compatible form in vivo. The expression "biologically compatible form suitable for administration in vivo" as used herein means a form of the substance to be administered in which any toxic effects are outweighed by the therapeutic effects. The substances may be administered to any animal, preferably humans.

The vaccines of the present invention may additionally contain suitable diluents, adjuvants and/or carriers. Preferably, the vaccines contain an adjuvant which can enhance the immunogenicity of the vaccine in vivo. The adjuvant may be selected from many known adjuvants in the art including the lipid-A portion of gram negative bacteria endotoxin, trehalose dimycolate of mycobacteria, the phospholipid lysolecithin, dimethyldictadecyl ammonium bromide (DDA), certain linear polyoxypropylene-polyoxyethylene (POP-POE) block polymers, aluminum hydroxide, liposomes and CpG (cytosine-phosphate-guanidine) polymers. The vaccines may also include cytokines that are known to enhance the immune response including GM-CSF, IL-2, IL-12, TNF and IFNγ.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

The vaccines of the instant invention may be formulated and introduced as a vaccine through oral, intradermal, intramuscular, intraperitoneal, intravenous, subcutaneous, intranasal, and intravaginal, or any other standard route of immunization.

In formulations of the subject vaccines, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any method well known in the art of pharmacy. The amount of composition that may be combined with a carrier material to produce a single dose may vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations, which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants, which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

In addition, vaccines may be administered parenterally as injections (intravenous, intramuscular or subcutaneous). The vaccine compositions of the present invention may optionally contain one or more adjuvants. Any suitable adjuvant can be used, such as CpG polymers, aluminum hydroxide, aluminum phosphate, plant and animal oils, and the like, with the amount of adjuvant depending on the nature of the particular adjuvant employed. In addition, the anti-infective vaccine compositions may also contain at least one stabilizer, such as carbohydrates such as sorbitol, mannitol, starch, sucrose, dextrin, and glucose, as well as proteins such as albumin or casein, and buffers such as alkali metal phosphates and the like.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers, which may be employed in the pharmaceutical compositions of the invention, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Further, non-cytolytic recombinant lentivirus of the present invention may be encapsulated in liposomes and administered via injection. Commercially available liposome delivery systems are available from Novavax, Inc. of Rockville, Md., commercially available under the name Novasomes™. These liposomes are specifically formulated for immunogen or antibody delivery. In an embodiment of the invention, Novasomes™ containing Isd peptides or antibody molecules bound to the surface of these non-phospholipid positively charged liposomes may be used.

5. Methods of Use

The present invention also features methods of preventing or treating a lentiviral infection in a subject comprising administering to the subject an effective amount of a vaccine.

The recombinant lentiviruses of the present invention can be prepared using techniques known in the art. In one embodiment, the lentivirus may be introduced in a host cell under conditions suitable for the replication and expression of the lentivirus in the host. Accordingly, the present invention also provides a cell transfected with a recombinant lentivirus wherein the natural signal sequence of the virus' envelope glycoprotein gp120 is modified to provide an essentially non-cytotoxic virus or is replaced with an essentially non-cytolytic signal sequence. The cell is preferably a T-lymphocyte, more preferably a T-cell that is not derived from a transformed cell line.

Accordingly, the present invention also provides a method of preventing or treating a lentiviral infection comprising administering an effective amount of a killed recombinant essentially non-cytolytic avirulent lentivirus of the present invention to an animal in need thereof. The term "effective amount" as used herein means an amount effective and at dosages and for periods of time necessary to achieve the desired result. The term "animal" as used herein includes all members of the animal kingdom including mammals, preferably humans.

In a preferred embodiment, the present invention provides a method of preventing or treating a lentiviral infection comprising administering an effective amount of a killed recombinant essentially non-cytolytic avirulent lentivirus to an animal in need thereof, wherein the natural signal sequence of the virus' envelope glycoprotein, preferably gp120, is modified to provide an essentially non-cytolytic signal sequence, preferably the virus is rendered avirulent by deleting the nef gene.

According to the aformentioned embodiment the modification to provide a non-cytolytic NSS results in no more than one positively charged amino acid in the NSS sequence. Most preferably, the animal is a human, preferably the lentivirus is HIV-1.

In a further preferred embodiment, the present invention provides a method of preventing or treating a lentiviral infection comprising administering an effective amount of a killed recombinant essentially non-cytolytic avirulent lentivirus to an animal in need thereof, wherein the natural signal sequence of the virus' envelope glycoprotein, preferably gp120, is replaced with an essentially non-cytolytic signal sequence, preferably the virus is rendered avirulent by deleting the nef gene. Most preferably, the animal is a human, preferably the lentivirus is HIV-1.

The present invention further includes a method of killing or destroying target cells, preferably cancer cells, comprising administering to the cell or cells, an effective amount of a recombinant virus, preferably vesticular stomatitus virus (VSV) or any other carrier RNA virus, specific for the target cells, containing, preferably the NSS of HIV-1.

Preferably the cells are in an animal in need thereof, most preferably in human. Cells which are infected or cancerous, express cell specific markers for which a complementary recognition site may be incorporated into a suitable vector into which the NSS of HIV-1 has been incorporated. This approach has been taken with vesicular stomatitis virus (VSV) which has been engineered to incorporate the genes for CD4 and CXCR4 thereby targeting the modified VSV to infect HIV-1 infected cells (Schnell, M. J. et al. Cell 90:849-857 (1997)). Accordingly, the present invention provides a method of killing target cells, such as cancer cells, comprising administering a recombinant virus containing NSS and a recognition site specific to the target cells, to an animal in need thereof. In an embodiment, the NSS of HIV-1 is incorporated into a modified VSV-like vector which has been targeted to a specific cancer cell type based on a particular cancer cell surface antigen thereby providing the VSV with the ability to induce apoptosis in the targeted cancer cells.

7. EXEMPLIFICATION

The following non-limiting examples are illustrative of the present invention.

Example 1a

Construction of Recombinant Baculoviruses

Construction of recombinant baculoviruses expressing Human Immunodeficiency Virus-1 glycoprotein 120 with its natural signal sequence (gp120-NSS), with its natural signal sequence replaced with a honey bee mellatin signal sequence (gp120-MSS), and with its natural signal sequence removed (gp120-ΔS) have been described previously by Li et al. (Virology 204:266-278 (1994)). Construction of recombinant baculovirus expressing vesicular stomatitis virus glycoprotein G (VSV$_{Ind}$G) was described previously by Bailey et al. (Virology 169:323-331 (1989)).

Construction of recombinant baculovirus expressing VSV$_{Ind}$ G protein with HIV-1 envelope glycoprotein gp120 signal sequence (VSV-G-NSS) is described below.

To replace the signal sequence of VSV-G protein, the present inventors first constructed VSV-G-ΔS (vesicular stomatitis virus glycoprotein G without its signal sequence) by PCR with two primers:

```
primer #1    5'-GGC GGA TCC GGA TCA ACG TTC ACC ATA GTT-3'   (SEQ ID NO: 9)
(5'primer)           BamH    SphI   +1VSV-G primer #2    5'-GGC GGA TCC TTA CTT TCC AAG TCG-3'           (SEQ ID NO: 10)
(3'primer)           BamHI   stop codon
``` primer #2 is complementary to C-terminus gene of VSV-G

The plasmid pwKl (which contains VSV$_{Ind}$ full-length G gene, and provided kindly by Dr. Robert R. Wagner, University of Virginia, U.S.A.) was used as the template, and amplified with the Geneamp kit by 30 cycles of PCR in a Perkin Elmer Cetus Thermocycler (the cycles were 94° C., 1 min; 45° C., 2 min; 72° C., 3 min) from 20 ng of pwKl as the template and 1.0 µM of each primer.

All primers had BamHI sites at their 5' terminus so that the amplified VSV-G-ΔS DNA fragment could be inserted into BamHI site of the plasmid, pBluescript SK VECTOR (Stratagene). The clone in which 5' terminus of VSV-G-ΔS toward T7 promoter was selected, and digested with SphI+XhoI restriction enzymes.

Example 1b

Site-Specific Mutagenesis by Polymerase Chain Reaction (PCR)

To change the positively charged amino acids located in the signal sequence of HIV-1 envelope gp120 into apolar amino acids, oligonucleotide-directed mutagenesis was performed by PCR in a Perkin-Elmer Cetus thermocycler. The four mutating oligonucleotide primers were designed to generate a series of mutations (YL-1, YL-2, YL-3, & YL-4) in the coding region of the HIV-1 envelope gp120 signal sequence are:

```
                                                    (SEQ ID NO: 11)
YL-1  5'-ATT TCG GAT CCT ATA AAT ATG AGA GTC GCG GAG
      ATA TAT CAT CAC-3'

(SEQ ID NO: 12)
YL-2  5'- ATT TCG GAT CCT ATA AAT ATG ATA GTC AAG
      GAG AAA TAT CAG CAC TTG TGG ATA TGG GGG TGG
      ATA TGG GGC-3'

(SEQ ID NO: 13)
YL-3  5'- ATT TCG GAT CCT ATA AAT ATG AGA GTC GTG
      GAG ATA TAT CAG CAC TTG TGG ATA TGG GGC-3'

(SEQ ID NO: 14)
YL-4  5'- ATT TCG GAT CCT ATA AAT ATG ATA GTG GCG
      GAG ATA TAT CAG CAC TTG TGG ATA TGG GGG TGG
      ATA TGG GGC-3'
```

The nucleotides underlined are the altered ones.

In addition, a universal primer (YL-5; 5'-AGC TTG GAT CCT TAT CTT TTT TCT CTC TGC TGC ACC-3' (SEQ ID NO: 15)) complementary to the C-terminus of the gp120 gene was used to obtain the full-length mutant gp120 clones. The gp120 encoding sequence was amplified with the Geneamp kit by 30 cycles of PCR (the cycles were 94° C., 1 min; 45° C., 2 min; 72° C., 3 min) from 20 ng of HindIII-linerized pUC19-gp120-NSS as a template and 1.0 µM of each mutant primer and the universal primer. All primers had BamH1 sites in their 5' terminus so that the amplified gp120 DNA fragment could be inserted into the BamH1 site of pAcYM1. All constructed mutants has the expected mutations verified by dideoxy chain-termination sequencing.

Example 1c

Amplification of HIV-1 Signal Sequence

The HIV-1 signal sequence of env gene was amplified from pBluescript-gp120-NSS by PCR with the following two primers:

```
primer #1                              (SEQ ID NO: 16)
(T7 primer)       5'-AAT ACG ACT CAC TAT-3' primer #2                              (SEQ ID NO: 17)
(complementary    5'-GGC GCA TGC ACT ACA GAT CAT-3'
SphI to                    Sph I
c-terminus of
HIV-1 signal
sequence gene)
```

The amplified DNA fragment containing HIV-1 signal sequence was digested with XhoI plus SphI restriction enzymes, and inserted into XhoI and SphI digested vector, pBluescript VSV-G-ΔS. The resulting plasmid is designated as pBSK VSV-G-NSS, and the construct was further confirmed by DNA sequencing.

The BamHI fragment of VSV-G-NSS was inserted into the BamHI site of a baculovirus pAcYM1 (Li, Y. et al. Virology 204:266-278 (1994)), and recombinant baculovirus expressing VSV-G-NSS was generated by standard transfection method (Li, Y. et al. Virology 204:266-278 (1994)).

Example 2

Microscopic Examination of Recombinant Baculoviruses Infected Cells

SF21 cells were infected with recombinant AcNPV at a m.o.i. of 5 PFU/cell and incubated at 27° C. for 48 hrs. The infected cells were examined by phase-contrast microscope. The results are shown in FIG. 1. These results demonstrate that the HIV-1 env signal sequence kills cells rapidly.

Example 3

Effects of the HIV-1 env Signal Sequence on Cell Death

I. Trypan blue assay: SF21 cells were infected with recombinant AcNPV at a m.o.i. of 5 PFU/cell for 1 hr, and the inoculum was removed and incubated with the complete medium TNM-FH containing 10% fetal bovine serum (FBS). At 24, 48, and 72 hrs after infection, cells were stained with trypan blue (GIBCO, BRL) for 5 min. and the cells were counted through the microscope and the percent of dead cells was determined by using the following formulae:

$$\frac{\text{Dead cells (stained)}}{\text{Viable cells (unstained)} + \text{Dead cells}} \times 100 = \% \text{ Dead Cells}$$

II. Lactate Dehydrogenase Release Assay (LDRA): The LDRA was performed according to the instructions of the manufacturer (Boehringer Mannheim Cytotoxicity Detection Kit). SF21 cells were infected with recombinant AcNPV at a m.o.i. of 5 PFU/cell for 1 hr. and the inoculum was removed and incubated with complete medium at 27° C., culture medium was collected at regular intervals of 12 hr. and centrifuged at 12,000 rpm for 1 min. The culture supernatant was diluted 10 fold and 100 µl of the supernatant was incubated with 100 µl of reaction mixture (cytotoxicity detection kit) for 30 min at room temperature. The absorbance of samples was measured at 490 nm by quantitating the formazen dye formed by using a microplate (ELISA) reader (Bio-Rad 550). The results of the trypan blue and lactate dehydrogenase release assays are illustrated in FIGS. 2A and 2B, respectively.

In conclusion, rgp120 and VSV-G with the HIV-1 env natural signal sequence kill cells much faster. Cells survive much longer without the HIV-1 env natural signal sequence or with mellitin signal sequence. The HIV-1 env natural signal sequence is responsible for rapid cell death.

Example 4

Examination of Apoptosis

I. Total DNA extraction method: SF21 cells ($3 \times 10^6$) were infected with recombinant AcNPV at a m.o.i. of 5 PFU/cell for 1 hr. The inoculum was removed and incubated with complete medium at 27° C. for 48 hr. Cells were pelleted at 2500 rpm for 10 min and extracted with TSE (10 mM Tris, pH 8.0, 1 mM EDTA, 1% SDS, to which proteinase K, to a final concentration of 70 μg/ml, was added). Then, samples were incubated for 2 hr at 37° C., and at the end of incubation NaCl was added to a final concentration of 1 M and then samples were incubated at 4° C. overnight. The DNA was extracted with phenol:chloroform (1:1) and with chloroform. Finally ethanol (100%) was added to precipitate the DNA (15 min at 80° C.) and the DNA precipitate was pelleted by microcentrifugation at 12,000 rpm for 15 min. The DNA pellet was washed once with 70% ethanol, re-suspended in TE (10 mM Tris, pH 8.0, 1 mM EDTA) with RNase A (50 μg/ml), and electrophoresed on 1.2% agarose gel and stained with ethidium bromide (N. Chejanovsky and E. Gershburg, Virology 209:519-525 (1995)). The results are illustrated in FIG. 3. The above results demonstrate that the HIV-1 env natural signal sequence induces apoptosis.

II. Extraction of Fragmented DNA: SF21 cells were infected with vAc-VSV-G (VSV-G) or vAc-VSV-G-NSS (VSV-G-NSS) at a m.o.i. of 5 PFU/cell and incubated at 27° C. for 48 hours. At 48 hours post-infection, these cells ($3 \times 10^6$) were pelleted at 2,500 rpm for 5 min and lysed in solution containing 10 mM Tris HCl (pH 8.0), 10 mM EDTA, and 0.5% Triton X-100, and centrifuged at 12,000 rpm for 25 min in an Eppendorf microcentrifuge to pellet chromosome DNA. The supernatant was digested with 0.1 mg of RNaseA per ml at 37° C. for 1 hr and then for 2 hr with 1 mg proteinase K per ml at 50° C. in the presence of 1% SDS, extracted with phenol and chloroform, and precipitated with cold ethanol. The precipitate was re-suspended in TE and subjected to electrophoresis on 11.5% agarose gel containing 5 μg of ethidium bromide per ml. DNA was visualized by UV transillumination (Rosario Leopardi and Bernard Roizman, Proc. Natl. Acad. Sci. USA 93:9583-9587 (1996)). The results are shown in FIG. 4.

Example 5

Construction of Recombinant HIV-1 Containing Partial vpu and nef Deletion and NSS Substitution I. Construction of plasmid pNL4-3 containing the NSS substitution (with MSS, IL-3 or any other signal sequences) and vpu deletion: An infectious HIV-1 pro-viral DNA clone, pNL4-3 (provided by Dr. Malcolm Martin through the AIDS Research and Reference Reagent program, Division of AIDS, NIAID, NIH; Adachi, et al J. Virol. 59:284-291 (1986)) contains two unique restriction enzyme sites: EcoRI (position 5744) and BamHI (position 8466). The env gene encoding region starts from position 6221 and ends at position 8785. To replace the natural signal sequence of HIV-1 env with mellitin, IL-3 or any other secretory protein signal sequences, the EcoRI–BamHI fragment of pNL4-3 is isolated from agarose gel and sub-cloned into the EcoRI-BamHI site of pBluescript SK (pBSK) vector. From this product, four primers are designed as follows:

```
primer #1 (Forward):
5'- GGC GAA TTC TGC AAC AAC TGC TG - 3'                      (SEQ ID NO: 18)
        EcoRi primer #2 (Reverse):
5'-GGC CTG CAG TCA TTA GGC ACT GTC TTC TGC TCT TTC-3'     (SEQ ID NO: 19)
        PstI  Stop codons primer #3 (Forward):
5'-GGC CTG CAG CCA TGG ACA GAA AAA TTG TTG GTC ACA GTC-3'  (SEQ ID NO: 20)
        PstI   NcoI primer #4 (Reverse):
5'-GGC GGA TCC GTT CAC TAA TCG AAT GG-3'                   (SEQ ID NO: 21)
       BamHI
```

The pBSK-env as template plus primers #1 and #2 are used and PCR is performed to amplify the left portion of env region, 477 bp fragment. Similarly, primers #3 and #4 are employed to amplify the right portion of env, 2245 bp. The EcoRI-PstI PCR product (477 bp fragment) was digested with EcoRI+PstI whereas the PstI-BamHI PCR product (2245 bp fragment) was cut with PstI+BamHI. Then, the PstI-BamHI digested 2245 bp fragment was cloned into the PstI+BamHI sites of pBSK vector.

Following this, the pBSK-2245 was digested with EcoRI+PstI and ligated with the EcoRI+PstI digested PCR products (445 bp fragment) resulting in the plasmid pBSK-env-ΔS.

The plasmid pBSK-env-ΔS was digested with PstI+NcoI and then ligated with the synthetic oligonucleotide encoding MSS signal sequences, IL-3 signal sequences, mutated natural signal sequences or any other desired signal sequences. This synthetic oligonucleotide contains a PstI site at 5' end and a NcoI site at 3' end. Before ligation into the vector, these double strand oligonucleotides were first digested with PstI+NcoI.

Synthetic oligonucleotide encoding mellitin signal sequence (only the positive sense is shown):

```
           PstI
5'-GGC CTG CAG ATG AAA TTC TTA GTC AAC GTT GCC CTT GTT TTT ATG GTC   (SEQ ID NO: 22)
GTG TAC ATT TCT TAC ATC TAT GCG GAT CCA TGG GCC-3'
                                    NcoI
```

Synthetic oligonucleotide encoding interlukin-3 signal sequence (only the positive sense is shown):

```
           PstI
5'-GGC CTG CAG ATG CTG CTC CTG CTC CTG ATG CTC TTC CAC GGA CTC CAA   (SEQ ID NO: 23)
GCT TCA ATC AGT GGC GAT CCA TGG GCC-3'
                    NcoI
```

After sequencing to verify the correct modification, the plasmid was digested with EcoRI+BamHI to isolate the EcoRI–BamHI fragment, which was re-cloned into the EcoRI–BamHI sites of pNL4-3 pro-viral DNA vector. The resulting plasmid is designated pHIV-1-MSS (or pHIV-1-IL3SS).

In addition, during the above construction, the NSS is substituted with not only MSS or IL-3 signal sequence, but also created partial vpu gene deletion. The vpu encodes 82 amino acids and its 3' end overlaps with the signal sequence of HIV-1 env gene, about 28 amino acids. However, it is in a different reading frame (−1 reading frame). Studies have shown that the deletion of vpu or nef genes did not alter the virus replication in either chimpanzee PBMCs, human PBMCs, or in the B/T cell hybrid line CEMx174 (James, et. al AIDS Res. Human Retrovirus 10:343-350 (1994)). Therefore, during the PCR amplification of 455 bp-fragment of the left portion of env with primers #1 and #2, two stop codons were added just in front of the start codon of env genes which results in the deletion of 28 amino acids of vpu (see primer #2).

II. Construction of plasmid containing nef deletion: The nef gene coding sequence starts from position 8787 and ends at position 9407 in pNL4-3 pro-viral DNA clone. There are also two unique restriction enzyme sites: BamHI site at position 8466 in env gene and XhoI site at position 8887 in nef gene. To make the nef gene deletion, the plasmid HIV-1 MSS (or IL-3SS) was digested with BamHI and XhoI. The resulting 421 bp of BamHI-XhoI fragment was isolated and subcloned into the Bam HI-XhoI sites of pBSK vector.

Two primers were designed:

```
                  BamHI
Primer #5:  5'- GGC GGA TCC TTA GCA CTT ATC TGG-3'     (SEQ ID NO: 24)
(Forward)

XhoI
Primer #6:  5'- GCC CTC GAG TCA TTA ATA CTG CTC CCA CCC-3'   (SEQ ID NO: 25)
                     Stop codons
```

The nef gene encodes 260 amino acids according to the present design. Two stop codons were inserted at the XhoI site which results in the nef only coding 33 amino acids. After PCR amplification and BamHI+XhoI digestion, this 421 bp of PCR DNA fragment was cloned back into the BamHI–XhoI pHIV-1-MSS (or IL-3SS) vector. The resulting recombinant plasmid contains the NSS substitution and partial vpu and nef deletion, which is used for the vaccine test.

Example 6

Measurements of Viral Production

A3.01 cells were initially seeded into 6-well plates at a density of $1 \times 10^6$ cells/well and transfected with 10 μg of proviral DNA. At 3 days post transfection, and every 2 days following, cultures were harvested and cells split 1:2 into fresh media without the addition of supplemental, uninfected cells. Harvested culture supernatants were pooled at each timepoint shown and analyzed for the presence of p24 by ELISA as indicator of virus production. Cells infected with either the NL4-3$^{WT}$ or NL4-3$^{nef-}$ virus showed maximum virus production at 13 days post transfection, however cells showed high levels of CPE and cell numbers declined rapidly with cultures being discontinued by 17 days post transfection. Cells infected with either the NL4-3$^{SSR}$ or NL4-3$^{nef-/SSR}$ viruses however, showed minimal CPE and remained persistently infected up to 29 days post transfection, at which point cells did eventually succumb to virus-induced CPE and cultures were discontinued. NL4-3$^{WT}$ or NL4-3$^{nef-}$ virus cultures produced a maximum of $1 \times 10^2$ μg p24 while NL4-3$^{SSR}$ or NL4-3$^{nef-/SSR}$ viruses produced over $1 \times 10^6$ μg p24 in a single harvest. Results shown in FIG. 6.

Example 7

Measuring Infectivity

Following transfection of proviral DNA, cells were split every 2 days and samples of the culture supernatant collected and analyzed by p24 ELISA in order to monitor viral replication. To assess the infectivity of virus particles being produced, samples were further analyzed by MAGI assay at 8 days post transfection in both A3.01 and H9 cells, and the results standardized to represent the number of infectious viral particles present per ng of p24 protein. As shown above, the Env signal sequence replacement mutant (NL4-3$^{SSR}$) and combination nef-deleted/Env signal sequence replacement mutant (NL4-3$^{nef-/SSR}$) both possess substantially reduced infectivity, with the replacement mutant being approximately 2-fold to 3-fold less infectious than wild-type virus (NL4-3$^{WT}$), and the combination mutant exhibiting as much as a 50-fold decrease in infectivity as compared to the wild-type. Results shown in FIG. 7.

Example 8

Induction of Cytopathic Effect

H9 cells were infected at a multiplicity of infection 3 with each of the viruses indicated. Infections were allowed to proceed with cultures being split 1:2 every 2 days. At 6 days post infection, cells were examined by light microscopy and cytopathic effect (CPE) was observed. See FIG. 8. As shown, H9 cells infected with either the NL4-3$^{WT}$ or NL4-3$^{nef-}$ virus (both of which contain the natural Env signal sequence) exhibited a rapid onset of CPE including cell death and formation of large syncitia (black arrows). In contrast, cells infected with either the NL4-3$^{SSR}$ or NL4-3$^{nef-/SSR}$ viruses (which contain the mellitin signal sequence in place of the natural Env signal sequence) showed very little sign of CPE despite active HIV replication (as measured by HIV-1 p24 ELISA; not shown).

Example 9

Construction of gag-NE Chimeric Genes

We have constructed chimeric gag genes with a selection of V3 and C3 sequences from all major clades of HIV-1. We hypothesize that antibodies made against these multiple linear epitopes will be capable of interacting with not only the original V3 regions, but also with any minor variants that may have been generated by natural infection or those which are present in HIV, that are being naturally transmitted throughout the population. Both the V3 region of gp120 and Gag proteins contain the neutralizing epitopes (NE) as well as cytotoxic T-lymphocyte epitopes (TCE). These epitopes may be capable of functioning independently as immunogens. We have linked multiple V3 loop sequences to an HIV-2 gag sequence to provide a larger antigen for expression and to form virus-like particles (VLP) to increase the potential for the induction of cytotoxic effectors. Our strategy of linking multiple V3 epitopes is illustrated in FIGS. 9a and 9b.

We have constructed replication defective recombinant human adenovirus 5 (rAd) by inserting the gag-V3 and gag-TCE chimeric genes into the E1a region of Ad5. These recombinant Ad5 were amplified in the human 2P3 cells constitutively expressing E1a proteins (see Example 11).

Neutralizing antibodies have been shown to be directed not only to V3 domains but also to other regions of HIV-1 (Luo et al., Virology 179: 874, 1990). Interestingly, the cross-neutralization analysis of different viral isolates suggests that conserved patterns of neutralization may exist across subtypes of HIV-1. For example, some sera from one type of HIV-1 infected individuals neutralize all HIV-1 subtypes, irrespective of their clades. This demonstration of neutralization is a result of the conserved neutralization epitopes such as those present in gp41 (Muster, et al., J. Virol. 67: 6642, 1993), or those epitopes corresponding to the CD4-binding site in gp120 (Thali, M. et al., J. Virol. 66: 5635, 1992). Differential selection pressure, related to the emergence of HIV-1 variants is associated with long-term non-progression. Thus, the presence of these C3 regions of gp120 is likely to provide additional protection (Wang, W -K. Et al., Proc. Natl. Acad. Sci. 93: 6693, 1996). See FIG. 9c.

Example 10

Construction of a gag-TCE Chimeric Gene

HIV-specific CTL are thought to exert immunologic selection pressure in HIV-infected persons. However, only a few pieces of data regarding the effects of this constraint on viral sequence variation in vivo are available. We have selected major cytotoxic T-cell epitopes (TCE) of HIV-1 gp120, gp41, Nef, RT and Rev, and linked them to the HIV-1 gag gene, to create a chimeric gag-TCE gene, which can be expressed by a recombinant adenovirus. FIG. 10a shows construction of HIV-1 gag gene with two different TCEs from the gp120, two different TCEs from Nef and one TCE from gp41 from HIV-1$_{HXB2}$ strain. Furthermore, we have also constructed another HIV-1 gag-TCE chimeric gene which will express TCEs of RT, Tat and Rev proteins from HIV-1$^{HXHB2}$. We have constructed replication defective recombinant human adenoviruses (rAd) carrying these HIV-2 gag-NE and HIV-1 gag-TCE as a part of HIV/AIDS vaccine.

Example 11

Generation of Replication Defective Recombinant Adenoviruses Containing HIV-2 gag-NE and HIV-1 gag-TCE as a Part of HIV/AIDS Vaccine We have modified the terminal DNA sequences of the gene cassettes containing the coding sequences of HIV-2 gag-NE and HIV-1 gag-TCE flanked by the BamH1 restriction site in order to insert these genes into an adenovirus vector. The general protocols to be used for the manipulation of adenovirus vectors have been previously described (Graham, et al., J. Gen. Virol. 36: 59, 1977). We have used the simplified system for generating recombinant adenoviruses according to Graham and colleagues (He, T. -C. et al., Proc. Natl. Acad. Sci. USA. 95: 2509, 1998). This new technique requires minimum enzymatic manipulation, using homologous recombination in bacteria rather than in eukaryotic cells. We have adapted this new strategy and found that it is an extremely efficient system to generate recombinant adenoviruses. Replication defective recombinant adenovirus vectors with inserts of HIV-2 gag-NE or HIV-1 gag-TCE chimeric genes within the E1a region of human adenovirus (Ad5) have been constructed by using techniques we have previously employed. We have successfully generated three replication defective recombinant adenoviruses with HIV-2 gag-NE and two replication defective recombinant adenoviruses with HIV-1 gag-TCE. The expression of the HIV-2 Gag-NE chimeric protein and formation of Gag-NE virus-like particles have been identified by either immunoprecipitation and Western blot analyses using the anti-Gag antibody (Luo, L, Li, Y, and Kang C. Y. Budding and secretion of HIV Gag-Env virus-like particles from recombinant human adenovirus infected cells, Virus Research 92: 75-82, 2003).

The replication defective recombinant adenovirus carrying the HIV-2 gag-NE or HIV-1 gag-TCE chimeric genes in the E1a region of human adenovirus 5 were propagated in 293 cells that express the E1a protein constitutively. These recombinant adenoviruses replicate well in the 293 cells and it was easy to prepare 1012 plaque forming units (PFU) after CsCl purification.

Example 12

Prophetic Vaccination Protocol for the Testing of a Novel Prime-Boost HIV-1/AIDS Vaccine The test subjects for this vaccine study will be 18 male Rhesus macaques (Macaca mulatto).

I. Antigen and Adjuvant: The following antigens and adjuvant are used.

1. Whole-inactivated virus antigen: A genetically modified HIV-1 clade B (NL4-3$^{nef-/SSR}$) will be produced, purified and undergo AT-2 inactivation. For immunization, specified animals will receive 500 µg of antigen suspended in 500 µl PBS (formulated with 500 µl of CpG oligodeoxynucleotide (ODN) adjuvant).

2. Replication-defective recombinant Adenovirus (rAd): High-titre stocks of 5 recombinant Adenovirus vectors expressing the HIV-1 gag gene in association with a number of selected neutralizing and T-cell epitopes will be prepared and purified. For immunization, specified animals will recieve $1 \times 10^9$ pfu of each recombinant virus ($1 \times 10^9$ pfu×5 recombinant viruses=$5 \times 10^9$ pfu) in a total volume of 500 µl (formulated with 500 µl of adjuvant).

3. CpG oligodeoxynucleotide (ODN) adjuvant: Purified phosphorothioate oligodeoxynucleotides of the sequence 5'-TCGTCGTTTTGTCGTTTTGTCGTT-3' (SEQ ID NO: 26; sequence subject to change) will be purchased. 500 µg of this ODN will be suspended in a total volume of 500 µl PBS for formulation with each antigen described above.

II. Immunization: The animals will be divided into 3 groups (designated Group 1-3), with each group containing a total of 6 Rhesus macaques. The immunization schedule for each group of animals is listed below including time of inoculation, type and quantity of antigen/adjuvant, and route of intramuscular (i.m.) immunization.

Group 1
  Week 0—500 µl whole-inactivated virus antigen with 500 µl CpG adjuvant-i.m.
  Week 4—500 µl rAd antigen with 500 µl CpG adjuvant—i.m.
  Week 8—500 µl rAd antigen with 500 µl CpG adjuvant—i.m.
  Week 16—500 µl rAd antigen with 500 µl CpG adjuvant—i.m.

Group 2
  Week 0—500 µl rAd antigen with 500 µl CpG adjuvant—i.m.
  Week 4—500 µl rAd antigen with 500 µl CpG adjuvant—i.m.
  Week 8—500 µl rAd antigen with 500 µl CpG adjuvant—i.m.
  Week 16—500 µl whole-inactivated virus antigen with 500 µl CpG adjuvant—i.m.

Group 3
  Group 3 will act as the unimmunized control group for the purposes of these experiments.

III. Challenge: At 24 weeks post-immunization all animals will be challenged with mixture of 100 TCID$_{50}$ of SHIV$^{SF162-P4}$ and 100 TCID$_{50}$ of SHIV$^{89.6}$ by intravenous injection.

IV. Sample Collection: At weeks −1, 0, 4, 6, 8, 10, 16, 18 and 20 post-immunization (p.i.), blood will be collected and analyzed for immune response. At weeks 1, 2 and 5 post-challenge (p.c.) and monthly thereafter, blood will be collected and stored for viral load and immune response studies. At 24 weeks p.c., the animals will be euthanized and blood and tissues collected for the virus load and neutralizing antibody determination.

V. Immune Response Analysis: In order to assess the immune response generated by both vaccination, and during the challenge period all samples will be tested for the following:

1. Anti-HIV antibody production: Serum samples will be analyzed for level of anti-HIV-1 Env and Gag antibodies by Enzyme-linked immunosorbent assay (ELISA).

2. HIV-specific T-cell proliferation: HIV-1 specific T-cell proliferative responses will be measured using whole-inactivated HIV-1 as antigenic stimulant.

3. Cytotoxic T-lymphocyte assay: Antigen stimulated effector PBMC's will be assessed for HIV-1/SHIV specific cytotoxic activity.

VI. Protective Effect of Vaccination Analysis: In order to assess the ability of the vaccination protocol to protect against viral challenge, all samples taken p.c. will further be tested for the following:

1. Viral load (vRNA): Plasma samples will be analyzed for vRNA levels by a quantitative branched DNA assay.

2. CD4:CD8 T-cell ratio: Levels of both CD4 and CD8 T-cells will be monitored p.c. as a potential marker towards sAIDS.

3. Antibody neutralization assay: Heat-inactivated serum samples will be tested for their ability to inhibit entry of challenge virus into the sMAGI reporter cell line.

4. IFN-γ secretion: The number of IFN-γ secreting cells will be determined via ELISPOT assay.

5. Cytokine production: Induction of cytokine mRNA expression will be monitored via reverse transcriptase real-time PCR. The presence of the cytokines; IFN-α, IFN-β, Mx, IFN-γ, IL-2, IL-4, IL-12, IL-6, TNF-α, MIP-1α, MIP-1β, and MDC will be assessed.

8. EQUIVALENTS

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

9. INCORPORATION BY REFERENCE

All publications, patents and patent applications cited are herein incorporated by reference in their entirety to the same extent as if each individual publication, patent or patent application was specifically and individually indicated to be incorporated by reference in its entirety.

We claim:

1. A recombinant lentivirus having a glycoprotein 120 signal sequence, wherein said glycoprotein 120 signal sequence is selected from the group consisting of the polypeptide sequences listed as SEQ ID NO 3-6, or a functional fragment or variant thereof, wherein said functional fragment or variant thereof contains no more than one (1) positively charged amino acid.

2. The recombinant lentivirus of claim 1, wherein said functional fragment or variant thereof contains one positively charged amino acid.

3. The recombinant lentivirus of claim 1, wherein said recombinant lentivirus is rendered avirulent by deletion of a sufficient amount of the nef gene.

4. The recombinant lentivirus of claim 1, which is HIV-1.

5. The recombinant lentivirus of claim 1, wherein said recombinant lentivirus is rendered avirulent by deletion of a sufficient amount of the nef gene; and said recombinant lentivirus is HIV-1.

6. An immunogenic composition comprising a recombinant lentivirus having a glycoprotein 120 signal sequence, wherein said glycoprotein 120 signal sequence is selected from the group consisting of the polypeptide sequences listed as SEQ ID NO 3-6, or a functional fragment or variant thereof, wherein said functional fragment or variant thereof contains no more than one (1) positively charged amino acid.

7. The immunogenic composition of claim 6, wherein said functional fragment or variant thereof contains one positively charged amino acid.

8. The immunogenic composition of claim 6, wherein said recombinant lentivirus is rendered avirulent by deletion of a sufficient amount of the nef gene.

9. The immunogenic composition of claim 6, wherein said recombinant lentivirus is HIV-1.

10. The immunogenic composition of claim 6, wherein said recombinant lentivirus is rendered avirulent by deletion of a sufficient amount of the nef gene; and said recombinant lentivirus is HIV-1.

11. The immunogenic composition of claim 6, wherein said functional fragment or variant thereof contains one positively charged amino acid; and said recombinant lentivirus is rendered avirulent by deletion of a sufficient amount of the nef gene.

12. The immunogenic composition of claim 6, wherein said functional fragment or variant thereof contains one positively charged amino acid; said recombinant lentivirus is rendered avirulent by deletion of a sufficient amount of the nef gene; and said recombinant lentivirus virus is HIV-1.

13. The immunogenic composition of claim 6, wherein said vaccine further comprises an adjuvant.

* * * * *